United States Patent [19]

Welker

[11] 4,172,670

[45] Oct. 30, 1979

[54] LIQUID SAMPLE COLLECTION APPARATUS

[76] Inventor: Robert H. Welker, P.O. Box 138, Sugarland, Tex. 77478

[21] Appl. No.: 917,343

[22] Filed: Jun. 20, 1978

Related U.S. Application Data

[63] Continuation-in-part of Ser. No. 810,046, Jun. 27, 1977, abandoned.

[51] Int. Cl.² .............................................. B01F 7/26
[52] U.S. Cl. .................................... 366/332; 366/131
[58] Field of Search ............... 366/131, 190, 256, 269, 366/289, 295, 315, 331, 332, 333; 222/309

[56] References Cited

U.S. PATENT DOCUMENTS

| 1,493,610 | 5/1924 | Darrah | 222/309 X |
| 2,667,407 | 1/1954 | Fenske et al. | 366/332 X |
| 2,831,606 | 4/1958 | Alters | 366/332 X |
| 3,341,076 | 9/1967 | Wasilewski et al. | 222/309 X |
| 3,793,888 | 2/1974 | Rosenwald | 366/182 X |

FOREIGN PATENT DOCUMENTS

2162091  7/1972  Fed. Rep. of Germany ........... 366/332
758691  10/1956  United Kingdom ..................... 366/332

*Primary Examiner*—Philip R. Coe
*Attorney, Agent, or Firm*—Gunn & Lee

[57] ABSTRACT

A liquid sample collector is disclosed. It incorporates a cylinder having a piston therein to define a storage chamber. There is an inlet to the storage chamber. In the storage chamber, a stirring plate mounted on a rod agitates the sample to prevent stratification of the sample. It is mounted on a stirring rod which extends all the way through the chamber, the rod passing through a cylinder head at one end of the cylinder and through the piston. It is stirred by reciprocating the stirring rod. The piston is mounted on a piston rod and moves as controlled by a hydraulic system wherein it maintains a desired back pressure on the sample to avoid vaporization. An alternate embodiment is disclosed where both ends of the stirring rod are exposed to pressures which are reduced and equalized to prevent placing a force differential on the piston rod in the stirring device.

8 Claims, 2 Drawing Figures

LIQUID SAMPLE COLLECTION APPARATUS

This application is a continuation-in-part of previous application of Robert H. Welker, Ser. No. 810,046, filed June 27, 1977, which application was abandoned on June 21, 1978.

BACKGROUND OF THE DISCLOSURE

This disclosure is directed to a sample collection apparatus. Many petroleum or chemical products are priced according to the total volume delivered and the percentage constituents within that volume. Typically, the constituents will have differing values. One constituent will be more valuable than the other. A sampling apparatus is connected to the supply line, and it draws off samples at a proportional to flow. As sample is collected, it accumulates in a container of the sort disclosed herein. The sample may sit for a substantial period of time in all sorts of weather. In the summer, it will be exposed to elevated temperatures, while low temperatures may be experienced during the winter. There is always the possibility and, indeed, depending on the mix of chemicals, the likelihood that the sample will stratify during accumulation. The sample itself is typically broken down into smaller lots for analysis. The sample will typically be in the range of about one to ten liters, and the larger volumes are most unwieldy at the time of testing.

The present invention is directed to an improved sample collection apparatus which particularly enables the sample to be stirred. The constituent sample components are thus mixed together, thereby overcoming sample stratification. The sample is stirred by hand agitating a stirring rod which extends through the sample chamber. As the stirring plate is raised and lowered, it flushes the sample around the ends and creates internal turbulence to mix the sample.

The present invention has the particular advantage that the stirring rod extends all the way through the sample chamber. Because of this, it maintains a fixed displacement in the chamber. This avoids the build up of pressure should the rod not extend fully through the chamber. As more rod is inserted into the chamber, pressures would otherwise rise, and this is highly undesirable.

In an alternate embodiment of the present invention, the stirring rod extends all the way through the apparatus and is encapsulated in chambers adapted to operate at reduced pressures and ideally at equalized pressures. This avoids formation of a pressure or force differential acting across the stirring rod. Indeed, it is possible to impose such a pressure differential on the stirring rod that the rod cannot be easily reciprocated against that pressure.

BRIEF DESCRIPTION OF THE DISCLOSED APPARATUS

This apparatus incorporates a cylinder having a head at each end and a piston in the cylinder. This defines a hydraulic chamber on one side of the piston and a sample storage chamber on the other side. An inlet is connected to the sample storage chamber. A stirring plate is positioned in the sample chamber, and a rod extends fully through the sample chamber to provide fixed or constant displacement. The rod is attached to a stirring plate so that reciprocation of the rod mixes the sample in the chamber. A hydraulic motor is provided which controllably forces the piston against the sample, thereby creating a controlled back pressure so that the sample storage pressure is controlled. It is desirable to maintain that pressure typically above the flash point pressure of the lightest liquid in the sample.

In an alternate embodiment, the apparatus incorporates an upstanding lower chamber having a receptacle for receiving the lower end of the stirring rod when it reciprocates. This chamber is pressure-isolated and vents to the atmosphere. In like fashion, the upper end of the stirring rod extends into the atmosphere so that both ends of the stirring rod are exposed, and, more importantly, they are exposed to approximately equal pressure levels to thereby avoid the formation of a pressure differential acting across the stirring rod.

DETAILED DESCRIPTION OF THE ILLUSTRATED EMBODIMENT

Figure 1:
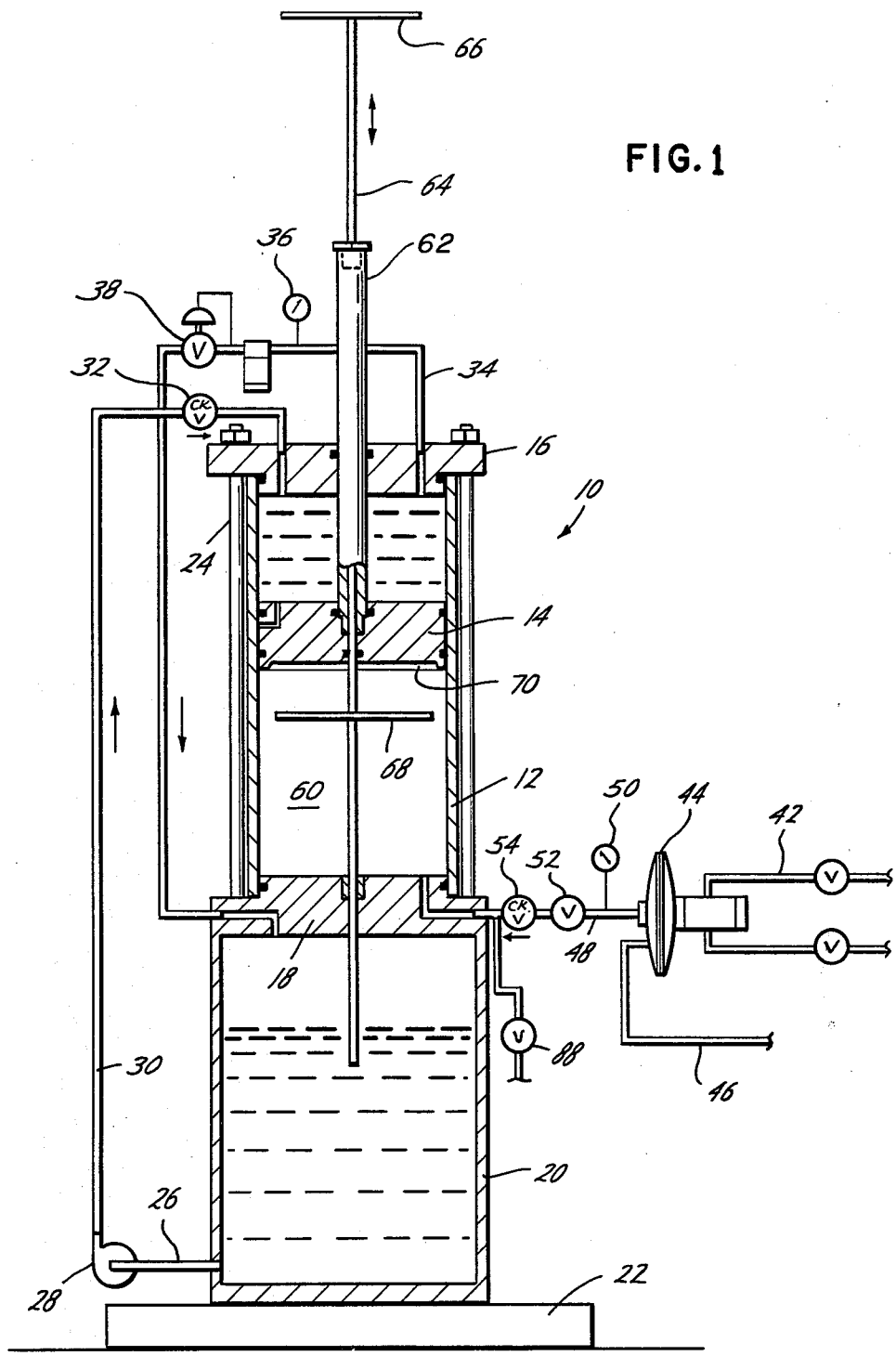
FIG. 1 is a sectional view through the sample storage and agitation apparatus disclosed herein and further includes the hydraulic system necessary for operation of the device.

In FIG. 1, the numeral 10 identifies the sample collection apparatus. A cylindrical shell 12 receives a piston 14 therein. The piston reciprocates slowly, and, accordingly, seal rings are included around its periphery to prevent leakage past the piston. The upper end of the cylinder is closed by a cylinder head 16, while the lower end is closed by a cylinder head 18. The head 18 is connected to a lower container 20 which serves as a hydraulic fluid sump. It is all supported on a suitable base or foundation 22.

The head 16 is held in position by stud bolts 24 which extend from the lower head 18 to the upper head 16. Both heads are sealed against the cylindrical shell 12 by suitable O-rings in O-ring grooves.

The container 20 receives a quantity of hydraulic oil and stores it. Oil is removed from it by a line 26 connected to a pump 28. The pump 28 delivers hydraulic fluid under pressure to a conduit 30. The conduit connects with a check valve 32. This prevents backward flow. The conduit 32 communicates through the head 16 into the upper chamber. Hydraulic fluid, under suitable pressure, fills that chamber and maintains a specified force on the piston 14. That force is controlled as will be described. Briefly, the head 16 receives another hydraulic conduit 34. If desired, a pressure gauge 36 is connected to the line 34. A pressure control valve 38 is placed in the line 34. The line 34 continues back to the sump to return surplus hydraulic fluid. The valve 38 is adjusted to control pressure on the piston. Adjustments are made at the valve as indicated on the gauge 36. Such adjustments are normally set so that the pressure on the piston on the hydraulic side is at least as great as the flash point pressure of the lightest liquid constituent in the sample. This prevents partial vaporization of the sample.

Continuing with the description of the apparatus, sample is collected from a suitable source. The source may be a storage tank, a flowing pipeline or the like. The numeral 42 identifies a fluid line connected to a flow diaphragm motor. The diaphragm motor 44 is adjusted on one side of the diaphragm. A supply line 46 from a suitable sample source is connected to the diaphragm motor 44. The diaphragm motor 44 is opened proportionately to a signal on a line 46 from some sort of command device; e.g., a proportionate to flow or clocked signal so that the sample is related to the measured product. The line 48 is optionally connected to a pressure gauge 50. It is also connected through a valve 52. The valve is opened or closed as required. Further, a check valve 54 prevents back flow. Line 48 opens into a sample chamber 60. The chamber 60 is on one side of the piston 14 and is defined by the piston head 18.

The piston 14 is mounted on a piston rod 62. The rod extends through the upper head 16 and a seal assembly to prevent leakage along it. The piston rod extends on the exterior of the equipment and serves as a marker to indicate the location of the piston. The piston rod 62 is axially hollow. A stirring rod 64 extends out the top end of the piston rod to a handle 66. The handle can be easily grasped and reciprocated. The stirring rod 64 passes fully through the piston rod 62 and the piston head 14. It supports a stirring plate having the form of a disk and identified at 68. The plate 68 is in the chamber 60. The piston 14 has a recessed or dished area 70 to enable the stirring plate 68 to seat against the piston head. The stirring rod is sufficiently long to pass fully through the chamber 60, a seal at the head 18, and its extra length extends below into the sump. The stirring rod 64 is of uniform cross section. This enables it to slide easily through the piston rod 62. Moreover, leakage along the stirring rod is prevented by suitable seals. The disk 68 is thus able to be reciprocated to and fro. As it is reciprocated, the outer edge causes the sample stored in the chamber 60 to flow with turbulence around the edge, thereby mixing the sample.

The present invention is used in the following manner. It ordinarily begins with the piston at the fully lowered position so that the chamber 60 has no sample in it. At this time, the valve 52 is closed, and the plate 68 is received in the recess 70. Typically, a sample is taken over a measured interval, such as one week or one month. The valve 52 is opened after the back pressure on the piston has been set. That setting is achieved at the valve 38. As an example, if the liquid to be sampled includes ethane and propane, approximately one thousand p.s.i. pressure must be maintained on the piston. The diaphragm motor 44 is set to some desired rate. Sample is gradually introduced into the chamber 60, and the piston 14 is forced upwardly in the cylinder 12. As it moves up, hydraulic fluid is forced from the upper chamber and is returned to the sump. Needless to say, the fluid flows as often as needed, being forced through the system by the pump 28 to maintain a required back pressure controlled by the pressure regulator 38.

Eventually, a full sample is taken. The size of the sample is observed by viewing the protrusion of the rod 62. At some suitable time, the sample can be removed. First, the sample valve 52 is closed, thereby ending the sample taking interval. As sample is slowly drawn off into a transport cylinder, the pump 28 is free to kick on and maintain the high back pressure. The sample is tapped at a valve 88. At the laboratory, the sample can be agitated at a convenient time. It is agitated by simple reciprocating movement on storage container similarly equipped with the handle 66 which stirs the disk up and down to mix the sample. After the sample has been thoroughly mixed, it can be removed under suitable laboratory control at elevated pressures to be analyzed. Thereafter, the piston 14 is restored to the down position, and another sample is subsequently taken. The rod 64 never varies displacement in the chamber 60, thus creating pressure resistant to the stirring action.

The device can be scaled to any suitable size, such as a sample chamber of one liter size. Five or ten liters can be taken, although this is somewhat larger. Larger samples are generally more unwieldy and, of course, require larger equipment. The sample collection apparatus of this disclosure is, of course, much heavier at that juncture.

Figure 2:
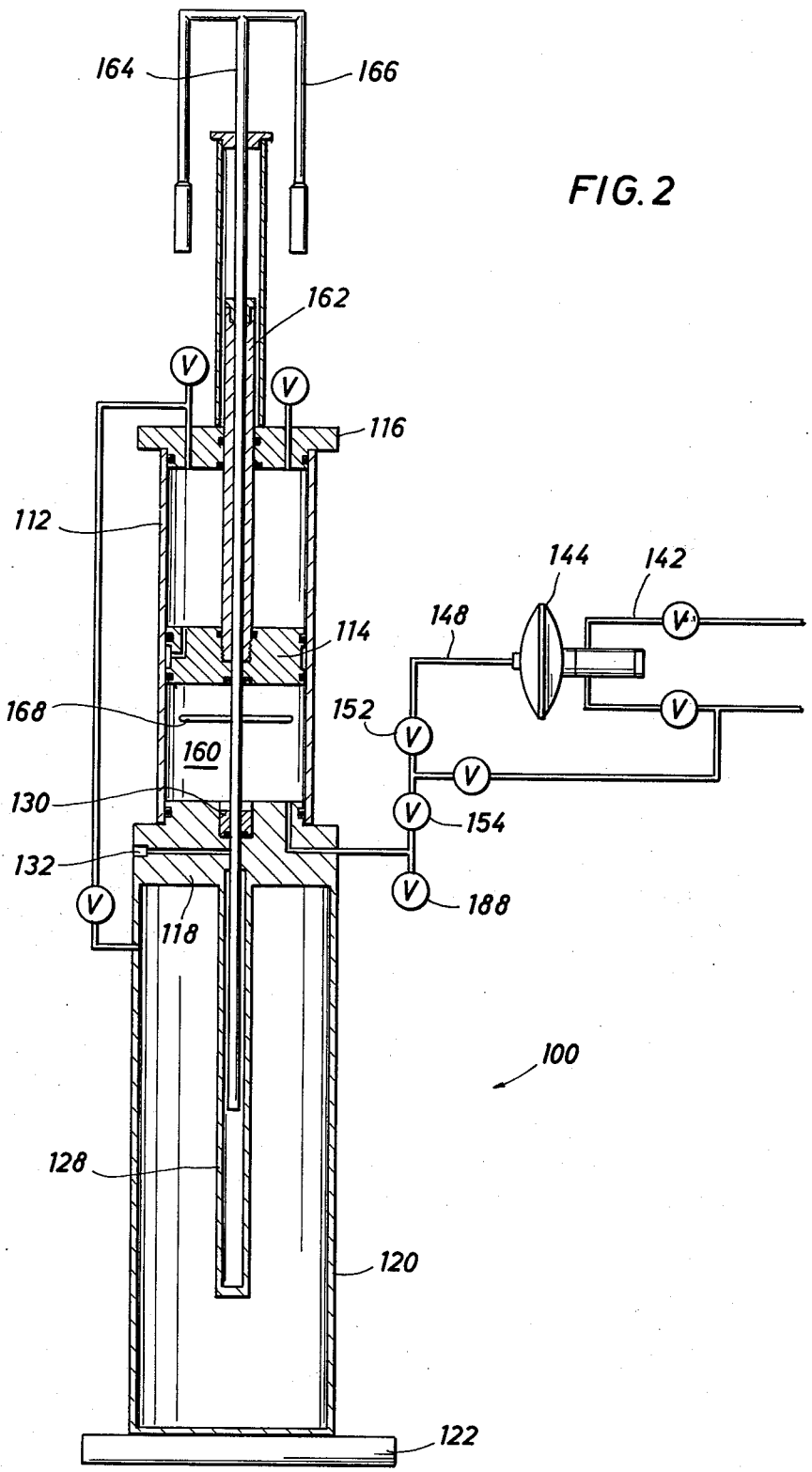
FIG. 2 is a sectional view through an alternate embodiment of the sample storage and agitation apparatus.

Attention is next directed to FIG. 2 of the drawings which discloses an alternate embodiment. FIG. 2 of the drawings is distinguished from the structure described in FIG. 1 in some regards. It is generally identified by the numeral 100. Similar components are identified with common reference numerals increased by 100. While the drawings are slightly different, it will be appreciated that these differences relate primarily to differences of scale and the like, and the equipment may be identical structurally and in the connections, or it may be different in scale, structure and such details.

In FIG. 2, the apparatus incorporates a cylindrical shell 112 with a piston 114 located in it. The piston is mounted on a piston rod 162. The piston rod extends through a cylinder head 116 at the top end of the equipment. Another cylinder head 118 is located at the bottom end of the cylinder and is very similar to the one shown in FIG. 1. It supports a lower chamber identified by the numeral 120, the apparatus sitting on a base 122. In like fashion, a stirring device 168 is located in the sample chamber 160. This mounts on a stirring rod 164 which extends through the full length of the piston rod 162 and is exposed at the upper end. The axial passage through the piston rod 162 is sealed, thereby preventing leakage along the stirring rod 164. The handle 166 at the upper end is equipped with a pair of handles bent over so that the device will be easily reached by an operator and will not stand so tall that the operator cannot reach it. This, of course, is necessary on large models but is not necessary on shorter models.

The present invention particularly modifies the lower chamber 120 by incorporation of a hollow, closed, tubular receptacle 128. The receptacle 128 is affixed to the lower side of the lower cylinder head 118. It is axially aligned so that the stirring rod 164 extends on its interior. The numeral 130 identifies a seal which prevents pressure from forcing sample fluid along the stirring rod. The pressure above the seal 130 may be as high as 1,000 psi., or some other level approximating the pressure of the sample source. The pressure below the seal is ideally atmospheric pressure. The chamber in the receptacle 128 is communicated to atmosphere through a lateral port or passage 132. This is below the seal 130. It will be appreciated that the stirring rod 164 has a specified cross-sectional area at the lower end and that this area is exposed to a pressure which acts on the stirring rod. Ideally, the pressure is as low as reasonable, preferably atmospheric pressure. This is achieved through the bleed passage 132. The passage 132 opens to the receptacle 128 below the seal 130.

By contrast, the upper end of the piston rod 162 supports the stirring rod 164 as it protrudes into space. Again, the stirring rod 164 is exposed to a particular pressure acting at its end, and, in this instance, the upper end is exposed to atmospheric pressure. This creates a differential force acting on the stirring rod, but, in this instance, the differential force is zero because both ends of the stirring rod are exposed to reduced and equalized pressures.

This pressure or force balance across the stirring rod avoids the situation where the stirring rod is forced out of the apparatus. This can occur where the pressure differential acting across the stirring rod is excessive. It is ideal to have the stirring disk 168 out of the way at certain times. However, when it is called into use, it is best that it be free of a differential pressure force acting across it.

The reduction in this differential force to a very small level, ideally to zero, is highly desirable. To this end, the stirring rod preferably has a constant cross-sectional area along its length. The constant cross-sectional area is made preferably uniform by utilizing the same stock of material in the fabrication of the stirring rod 164.

The device is used in the same manner as the embodiment 10. It is used by introducing a sample into the sample storage chamber 160 for subsequent stirring. However, stirring is accomplished in an improved fashion in that stirring can be achieved without working against excessive forces differentially formed across the stirring rod.

Little mention has been made of the sample delivery system shown in FIG. 2 because it is the same as that shown in FIG. 1. The significant point is that it is configured so that a specified sample is delivered at a specified rate for accumulation in the sample storage chamber 160.

The foregoing is directed to the preferred embodiment, but the scope thereof is determined by the claims which follow.

I claim:

1. A sample collecting apparatus for collecting and storing a liquid sample wherein the apparatus comprises:
    (a) a cylinder having a head means thereon;
    (b) a piston in said cylinder which defines a sample storage chamber in said cylinder;
    (c) inlet means connected to said sample storage chamber and which is adapted to be connected with a source of a sample to deliver a sample to said chamber;
    (d) a stirring plate having an encircling edge in said chamber and which plate is smaller than said chamber to enable said plate to fit within said chamber;
    (e) a stirring rod having two opposite ends connected to said stirring plate for positioning said plate in said sample storage chamber which plate extends into sample in said chamber to agitate sample around the edges of said plate on reciprocation of said rod, said stirring rod having a length sufficient to extend fully through said sample storage chamber to thereby maintain a fixed displacement of sample by said stirring rod and stirring plate within said sample storage chamber on reciprocation of said stirring rod; and
    (f) means operatively exposing the opposite ends of said stirring rod to a specified pressure differential acting across said stirring rod ends to form a differential force below a specified level across said stirring rod.

2. The apparatus of claim 1 including means for reciprocating said stirring rod.

3. The apparatus of claim 1 including a hydraulic motor operatively connected to said piston for providing a force acting on said piston to maintain a controlled back pressure on said sample storage chamber.

4. The apparatus of claim 1 including a piston rod connected to said piston and extending axially of said cylinder and through the head thereof to the exterior of said cylinder and wherein said stirring rod is axially positioned on the interior of said piston rod which is axially hollow.

5. The apparatus of claim 1 including seal means cooperative with said stirring rod and surrounding said rod and wherein said rod passes axially through an opening in said piston and also passes through an opening in said head means.

6. The apparatus of claim 1 including an open chamber on one side of a piston head means closing one end of said chamber and which open chamber has sufficient depth to enable said stirring rod to reciprocate freely in open space therein.

7. The apparatus of claim 6 including an axial passage along the full length of a piston rod connected to said piston.

8. The apparatus of claim 7 wherein said piston rod protrudes in the open for external viewing and said piston rod is larger in diameter than said stirring rod.

* * * * *